United States Patent [19]
Collins et al.

[11] Patent Number: 6,143,569
[45] Date of Patent: Nov. 7, 2000

[54] CHELATORS EXHIBITING TRIPLE FLUORESCENCE

[75] Inventors: Greg E. Collins, Waldorf; Ling-Siu Choi, Bethesda, both of Md.

[73] Assignee: The United States of America as represented by the Secretary of the Navy, Washington, D.C.

[21] Appl. No.: 09/144,106

[22] Filed: Aug. 31, 1998

[51] Int. Cl.[7] .................................................. G01N 33/20
[52] U.S. Cl. .............................. 436/73; 436/74; 436/79; 436/80; 436/81; 436/82; 436/83; 436/84; 540/450; 558/411; 564/305
[58] Field of Search .................. 436/73, 74, 79–84; 540/450, 467, 470, 471, 473, 474, 476; 558/411; 564/305, 368, 374

[56] References Cited

U.S. PATENT DOCUMENTS

| | | | |
|---|---|---|---|
| 3,752,810 | 8/1973 | Stahle et al. | 260/247.5 R |
| 5,034,411 | 7/1991 | Almgren et al. | 514/522 |
| 5,296,485 | 3/1994 | Lubisch et al. | 514/316 |
| 5,726,177 | 3/1998 | Halazy et al. | 514/253 |

FOREIGN PATENT DOCUMENTS 2-155961  6/1990  Japan.

OTHER PUBLICATIONS

W. Steinmann et al. Helv. Chim. Acta 1975, 58, 1358–1366.
A. P. Leugger et al. Helv. Chim. Acta 1978, 61, 2296–2306.
R. D. Hancock et al. J. Chem. Soc. Dalton Trans. 1987, 2911–2915.
R. D. Hancock J. Chem. Educ. 1992, 69, 615–621.
J.–F. Letard et al. Recl. Trav. Chim. Pays–Bas 1995, 114, 517–527.
G. E. Collins et al. J. Am. Chem. Soc. 1998, 120, 1474–1478.

*Primary Examiner*—Arlen Soderquist
*Attorney, Agent, or Firm*—Barry A. Edelberg; John J. Karasek

[57] ABSTRACT

A polyfunctional amine, such as cyclam, substituted with 4-(N,N-dimethylamino) benzonitrile, exhibits triple fluorescence and complexes with metal ions. The complexation of metal ions with the fluorophore changes the triple fluorescence characteristics of the fluorophore. Thus, this substituted polyfunctional amine provides an effective indicator for the qualitative and quantitative detection of metals.

20 Claims, 4 Drawing Sheets

DMABN

CNP3NM

DMABN-Crown4

DMABN-Cyclam

CHELATORS EXHIBITING TRIPLE FLUORESCENCE

BACKGROUND OF THE INVENTION

1. Field of the Invention

The present invention relates generally to chelators and more specifically to fluorescent chelators.

2. Background of the Invention

Description of the Background Art

The use of fluorescence to detect metals provides a convenient way to measure low concentrations of metals. Generally, a sample is exposed to a fluorescent chelating agent that preferentially complexes with the metal of interest, either shifting or greatly enhancing the fluorescence of the complexed ligand. However, these fluorescent chelates may be subject to interference resulting in unreliable results and rarely exhibit the ability to preferentially distinguish between various related metals.

The dual fluorescence of 4-(N,N-dimethylamino) benzonitrile, DMABN (FIG. 1a), in polar solvent was discovered by Lippert more than 30 years ago. Lippert et al, Angew. Chem., 1961, 73, 695. Several models have been proposed to address the cause for the unexpected, red-shifted fluorescence band which is apparent in addition to the normal, fluorescent emission of the locally excited state (LE). Grabowski et al proposed the twisted intramolecular charge transfer (TICT) state to successfully account for the red-shifted fluorescence. Grabowski et al, Pure Appl. Chem., 1983, 55, 245. TICT refers to the state wherein an intramolecular charge transfer takes place between the dimethyl amino donor group and the benzonitrile acceptor that is accompanied by a twisting motion and orbital decoupling of the phenyl acceptor ring from the dimethyl amino donor group. The TICT state has been observed in other molecular systems bearing donor and acceptor groups covalently linked. When the N,N-dimethylamino group in DMABN is replaced by an amino propyl group, the resulting compound, 3-(4-cyanophenyl)-1-N,N-dimethylamino-propane, forms an intramolecular exciplex between the phenyl and amino end groups. The formation of an intramolecular exciplex results from the flexibility of the alkyl chain, which links the donor and acceptor moieties close enough spatially, that a charge transfer step is possible.

Research has been conducted toward the development of fluorescent sensor molecules capable of sensitively and selectively monitoring heavy metal ion concentration. The covalent attachment of benzonitrile to the aza group of a metal binding ionophore that uniquely combines the properties of DMABN with the metal binding properties of metal binding ionophore has been considered as one way to accomplish this goal. For example, Létard et. al., Recl. Trav. Chim. Pays-Bas, 1995, 114, 517–527, reported the dual fluorescence of 4-(1-aza-4,7,10-trioxacyclododecyl) benzonitrile (DMABN-Crown4, FIG. 1c) and 4-(1-aza-4,7,10,13-tetraoxacyclopentadecyl)benzonitrile (DMABN-Crown5).

Benzonitriles bearing flexible, alkyl amino chains, e.g. 3-(4-cyanophenyl)-1-N,N-dimethylaminopropane (CNP3NM, FIG. 1b), can form intramolecular exciplexes which arise due to the conformational flexibility of the alkyl amino chain, and its ability to form a sandwich configuration promoting excited state, charge transfer (Grabowski, Z. R. Pure & Appl. Chem., 1992, 64, 1249–1255). The propensity for intramolecular exciplex formation in CNP3NM is indicated by the strong, red-shifted fluorescence observed, and the complete absence of LE emission. In contrast to TICT state formation, the large distance and minimal mesomeric interaction apparent between D and A causes a localized excited (LE) state precursor to be formed, wherein the excited state is primarily localized on either D or A, depending upon which gives the lower $S_1$ energy. Van der Auweraer et. al., J. Phys. Chem., 1991, 95, 2083–2092, observed a correlation between intramolecular exciplex formation and Hirayama's rule (Hirayama, F. J. Chem. Phys., 1965, 42, 3163–3171), which states that the most stable sandwich conformation will arise when n=3 for a phenyl-$(CH_2)_n$-$NMe_2$ system.

SUMMARY OF THE INVENTION

Accordingly, it is an object of this invention to provide fluorescent molecules for the detection of metals.

It is a further object of this invention to provide fluorescent molecules that alter their fluorescent characteristics upon chelation or complexation with a metal.

It is an additional object of the present invention to provide fluorescent molecules which exhibit triple fluorescence, and which exhibit peak shifts when complexed or chelated with a metal.

It is a farther object of the present invention to allow for the possibility of using fluorescence to simultaneously determine the concentration of various metals within a mixture of metal ions These and additional objects of the invention are accomplished by complexation or chelation of a metal with a novel fluorophore of the formula:

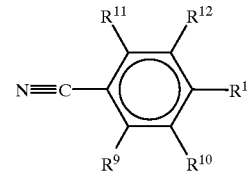

wherein $R^1$ is:

an aliphatic group bearing at least one nitrogen substituted by the benzonitrile group, at least one nitrogen 2 to 4 carbon atoms from the benzonitrile-substituted nitrogen, and at least one additional heteroatom selected from the groups consisting of N, O, and S, or an azacyclo group having at least two ring nitrogens, at least one of the ring nitrogens being substituted by the benzonitrile group and at least one of the ring nitrogens being 2 to 4 carbon atoms from the benzonitrile-substituted ring nitrogen, the azacyclo group having as ring members at least one additional heteroatom selected from the group consisting of N, O, and S, said at least one additional heteroatom having at least 2 carbons between it and the nearest of other ring member heteroatoms; and $R^9$, $R^{10}$, $R^{11}$, and $R^{12}$ are H or $CH_3$ and may be the same as or different from each other. In this specification and the claims that follow, the terms "ring member", "ring nitrogen", or "ring heteroatom" are used to distinguish those atoms, which constitute part of the azacyclo ring structure, from atoms which are merely part of a pendant group attached to the azacyclo ring structure.

BRIEF DESCRIPTION OF THE DRAWINGS

A more complete appreciation of the invention will be readily obtained by reference to the following Description of the Preferred Embodiments and the accompanying drawings, wherein.

DESCRIPTION OF THE PREFERRED EMBODIMENTS

Figure 2:
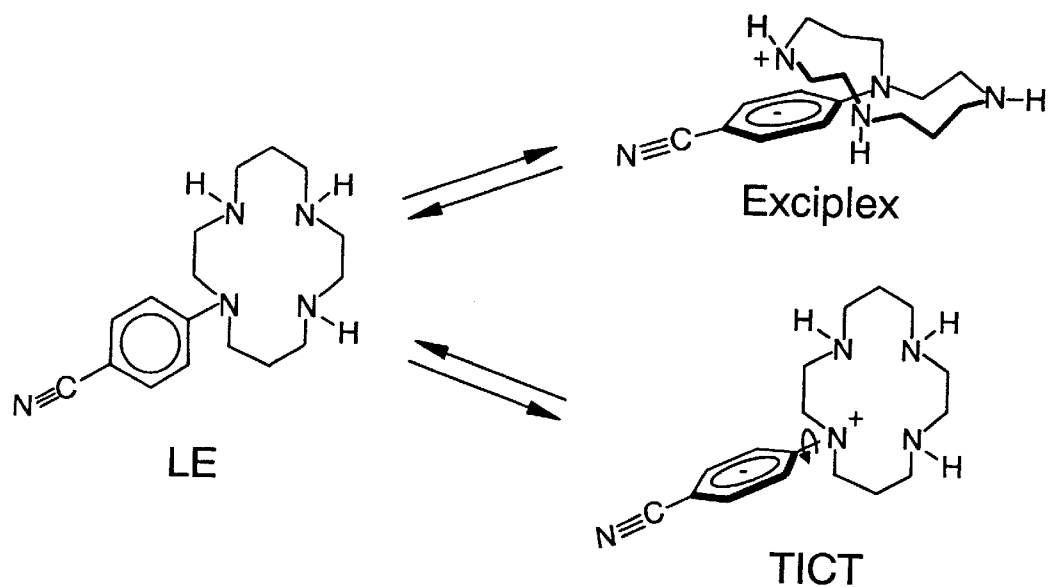
FIG. 2 shows proposed structures and equilibria existing between the three excited-state species generating the observed triple fluorescence of DMABN-Cyclam.

The novel fluorophore of the present invention exhibits three fluorescence peaks, i.e., triple fluorescence. As shown in FIG. 2, this triple fluorescence arises from the equilibria existing between three excited states species: LE, TICT, and an intramolecular exciplex (E) formed between the phenyl and amino end groups. The formation of an intramolecular exciplex results from the flexibility of the alkyl chain, which links the donor and acceptor moieties close enough spatially, that a charge transfer step is possible.

Complexation of the fluorophore with a metal changes the equilibria between these states, thus perturbing the triple fluorescence peaks. Also, complexation of the fluorophore with a metal red-shifts these peaks about 5 to about 10 nm. The type of peak permutation observed and amount of red-shifting depends upon the complexed metal, the solvent system used, and the concentration of metal in the solution.

The concentration of the fluorophore in solution is not critical, provided that the solution has a sufficient concentration of fluorophore to generate detectable fluorescence, and provided that the solution is sufficiently dilute to avoid the formation of intermolecular, rather than intramolecular, exciplexes. These concentrations may be determined empirically for any given combination of metal, fluorophore and solvent.

The fluorophore of the present invention may be used in both polar and non-polar, protic and aprotic solvents. Typical solvents with which the compound of the present invention may be used include ethanol, acetonitrile, $H_2O$, and mixtures (particularly solutions) thereof. In general, polar solvents tend to red shift the TICT emission band and to increase the intensity of the TICT emission band relative to the E and LE emission bands, since those solvents stabilize charge separation and an open geometry. Conversely, non-polar solvents cannot stabilize charge separation, thus increasing the intensity of the LE emission band relative to the TICT and E emission bands.

In aqueous solvents, the relative intensities of the peaks also varies with pH. Up to pH 3, exciplex formation and emission band intensity generally increase with increasing pH, at which point exciplex formation is at a maximum. Above pH 3, exciplex formation and emission band intensity steadily decrease. Up to pH 3, TICT formation and emission band intensity generally increase. At pH 3, TICT formation and emission band intensity is generally nearly level. Above pH 8, TICT formation and emission band intensity steadily decline. Generally, LE formation and emission band intensity steadily decrease with increasing pH, ultimately leveling off at pH 8 and above.

The fluorophore of the present invention selectively complexes transition metal ions, heavy metal ions, and mixtures thereof. Typical metals complexed by the fluorophore of the present invention include Zn(II), Cd(II), Cu(I), Cu(II), Ni(II), Pb(II), Hg(II), Fe(III), Al(III), and mixtures thereof. Complexation of the fluorophore of the present invention perturbs the intensities and positions of the three fluorescent peaks, by stabilizing or destabilizing the configurations that give rise to those emissions. The nature and degree of this permutation depends upon both the solvent system employed and the complexed metal ion. Generally, in highly protic solvents (e.g., aqueous solvents) such as water at pH=7, complexation with metal ions causes a net decrease in TICT and E state emission. Concurrently, in such solvents, complexation of the fluorophore of the invention with metal ions increases LE emission, provided that the metal ions do not cause intracomplex quenching of LE emission. Complexes of the fluorophore of the present invention with $Zn^{2+}$ and $Cd^{2+}$ exemplify this behavior, causing an increase in LE emission. Complexation of the fluorophore of the present invention with large, paramagnetic, or easily reducible cations, such as $Hg^{2+}$, $Pb^{2+}$, $Cu^{2+}$, and $Ni^{2+}$, however, decreases the observed LE emission, due to intracomplex quenching of LE emission.

The effects of metal complexation of the fluorophore upon various emission bands differs when an aprotic solvent, such as acetonitrile, or an organic solvent, such as ethanol, are employed. Generally, in these solvents, complexation of the fluorophore of the present invention with metal ions increases exciplex emission. Typically, TICT emission decreases, and LE emission increases, upon complexation of the fluorophore with a metal ion in an aprotic or organic solvent. In some cases, however, such as complexation of the fluorophore with $Hg^{2+}$, LE emission may be reduced by the quenching behavior of a large, easily reducible ion. Additionally, the presence of uncomplexed paramagnetic ions, such as $Cu^{2+}$, after complexation of the fluorophore in solutions having greater than the stoichiometric concentration of the ion, may result in diffusional quenching of the fluorophore:metal ion complex.

The effects of metal complexation of the fluorophore of the present invention upon fluorescent emission at three separate emission bands, and in different solvents, or mixtures of solvents, allows the fluorophore of the present invention to detect the presence of a large variety of metals in a variety of different environments. For example, in environments where emission changes in the TICT or LE emission bands, caused by complexation of the fluorophore with a metal ion, or quenched by surrounding molecules, or otherwise difficult to detect, the presence of the metal ion may be determined by monitoring the E emission band.

Also, the unique effects of metals upon the positions and intensities of the three fluorescence peaks allows for the possibility that the results may be analyzed and evaluated heuristically to determine, either alone or with test results from other analytical procedures, the metal ion compositions of solutions containing several metal ions.

The characteristics of the fluorophore of the present invention will also depend, to some extent, upon its exact composition. For example, the benzonitrile component of the present invention may be unsubstituted or substituted with methyl groups, if desired, in the meta and ortho positions. The electron-donating character of the methyl groups should increase the stability of the exciplex, but may also sterically hinder exciplex formation. Thus, typically, at least one of $R^{10}$ and $R^{12}$ will be H. The use of an aliphatic group for $R^1$, rather than an azacyclo group should enhance exciplex formation because of its additional stability. However, aliphatic groups tend to form weaker complexes with metals than do azacyclo groups.

In $R^1$, at least one nitrogen (referred to herein as the neighboring nitrogen) should be located within 2 to 4 carbons of the nitrogen bearing the pendant benzonitrile group (i.e., the benzonitrile-substituted nitrogen). In the exciplex configuration, the neighboring nitrogen bears a $\delta^+$ charge. If the neighboring nitrogen is less than two carbons from the benzonitrile-substituted nitrogen, the limited flexibility of the carbon chain hinders exciplex formation. If the neighboring nitrogen is more than four carbons from the benzonitrile-substituted nitrogen, the large size of the carbon chain sterically hinders exciplex formation. To allow for efficient metal binding, $R^1$ includes at least one additional heteroatom, typically spaced 2 to 4 carbon atoms from the closest heteroatom. More often, the heteroatoms of $R^1$ are spaced 2 or 3 carbon atoms from each other.

Generally, although additional heteroatoms improve metal complexation, the additional bulk and structural limitations that arise when more than two additional heteroatoms are present may hinder exciplex formation, depending upon the position of the additional heteroatoms relative to the benzonitrile-substituted nitrogen and the neighboring nitrogen. Typically, $R^1$ having from 1 to 5 heteroatoms in addition to the benzonitrile-substituted nitrogen and the neighboring nitrogen strikes the best balance between metal complexing ability and exciplex formation. Any additional nitrogen heteroatoms in $R^1$ may be substituted with aliphatic groups that are substituted or unsubstituted. Except for obvious steric hindrances (which depend upon the location of the aliphatic groups relative to the benzonitrile-substituted and neighboring nitrogens and the heteroatoms which complex the metal), and charge stability effects (which depend upon the distance of any electron-donating or electron-withdrawing moiety in the aliphatic group from the benzonitrile-substituted and neighboring nitrogens and the heteroatoms which complex the metal), the nature of the aliphatic group and substitutions thereof should have at most a minor effect on the complexing and triple fluorescence properties of the fluorophore of the present invention. Generally, atoms more than 4 carbons from the benzonitrile-substituted and neighboring nitrogens and the heteroatoms which complex the metal have a minimal impact on these properties.

In addition to the varying the number of heteroatoms, the nature of the additional heteroatoms can also be varied to allow for greater differentiation between or preferential complexation among various metals. In most cases, however, $R^1$ includes 3 or 4 nitrogens, and usually 4 nitrogens.

Typically, $R^1$ has one of the following structures:

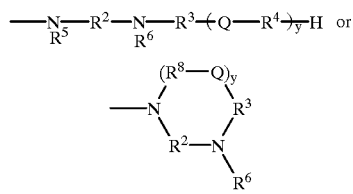

wherein $R^2$ and $R^3$ are unsubstituted $C_2$ to $C_4$ alkylene groups or $C_2$ to $C_4$ alkylene groups substituted with an aliphatic group, and may be the same as or different from one another;

$R^4$ is -, an unsubstituted $C_2$ to $C_4$ alkylene group, or a $C_2$ to $C_4$ alkylene group substituted with an aliphatic group, and may be the same or different from any other $R^4$ groups present and may be the same or different from $R^2$ and $R^3$;

Q is NH, $NR^7$, O, or S, and may be the same as or different from any other Q group present;

$R^5$, $R^6$, and $R^7$ are aliphatic groups and may be the same as or different from each other;

$R^8$ is an unsubstituted $C_2$ to $C_4$ alkylene group or a $C_2$ to $C_4$ alkylene groups substituted with an aliphatic group, and may be the same as or different from any other $R^8$ group present; and y is an integer having a value of from 1 to 5.

As can be seen from the above formula, in azacyclo structures, the ring size may be varied. Typically, the ring includes 3 or 4 heteroatoms. Most often, the ring includes 4 heteroatoms.

Metal ion concentration in liquids can be quantitatively and qualitatively detected using the fluorophore of the present invention. Quantitative detection can be accomplished when sufficient fluorophore is available to complex with all metal ions present. The degree of fluorescent signal perturbation will be proportional to the metal ion concentration. This detection can be accomplished by determining the extent of emission frequency shifting and/or intensity change caused by complexation for one, two, or all of the excited states responsible for fluorescent emission (TICT, LE, and E). The extent of emission frequency shifting and/or intensity change may be determined directly by comparison with a blank or concurrently analyzed standard solutions, or may be indirectly determined by reference to a chart or other data based on previously analyzed standard solutions.

The triple fluorescence of the fluorophore of the present invention increases its versatility. For example, if the fluorescent emission of one excited state is quenched by an interfering compound, the metal may still be detected by examining the fluorescent emission of the other excited states.

Having described the invention, the following examples are given to illustrate specific applications of the invention including the best mode now known to perform the invention. These specific examples are not intended to limit the scope of the invention described in this application.

EXAMPLES

Based upon the general procedure given by Suhr, *Liebigs Annalen*, 1965, 687, 175–182 (the entirety of which is incorporated by reference for all purposes), DMABN-Cyclam (FIG. 1d) was prepared via the nucleophilic aromatic substitution of 4-fluorobenzonitrile with 1,4,8,11-tetraazacyclotetradecane (Cyclam) in DMSO at 130° C. under argon for four days. Following room temperature filtration, DMSO was removed under vacuum, and the resulting yellow solid redissolved in toluene and purified via silica gel column chromatography. Sequential elution of the compound with toluene, isopropanol and 20% concentrated NH$_4$OH in ethanol separated the product. UV, $\lambda_{max}$=295 mn; $^1$H NMR(CD$_3$CN) δ 1.68 (m,4, CH$_2$CH$_2$CH$_2$), 2.65 (s,3, NH),2.72 (m, 12, CH$_2$NH), 3.47 (m, 4, CH$_2$NAr), 6.66 (d, 2, ArH), 7.38 (d, 2, ArH); $^{13}$C NMR (CD$_3$CN) δ 27.83, 28.05, 45.72, 47.18, 47.80, 48.29, 48.72, 48.89, 49.21, 51.33, 96.85, 112.60, 121.16, 133.93, 152.57; electrospray MS, (M+H$^+$) 302.4; calcd for C$_{17}$H$_{27}$N$_5$+H$^+$, 302.4.

A Spex Fluorolog τ2 spectrofluorimeter was used for making all fluorescence measurements, and a double-beam Hitachi U3000 spectrophotometer was used for all absorbance measurements. The excitation wavelength used was 295 nm. The solvents were of spectral grade quality and used as received from the supplier (Aldrich or Fischer Scientific). All metal salts contained chloride anions and were of the highest purity available (Aldrich or Alfa). Buffers (0.1 M) were prepared using H$_3$PO$_4$ (pH 1–3), acetic acid (pH 4–5), NaH$_2$PO$_4$ (pH 6–8), NaHCO$_3$ (pH 9–11), Na$_2$HPO$_4$ (pH 12), and NaOH (pH 13), with the pH being adjusted using either HCl or NaOH while monitoring with a pH meter. Intensity contributions from the three individual excited states were estimated using the Voigt Amplitude function of Jandel's PeakFit 4.0.

RESULTS AND DISCUSSION

Figure 3:
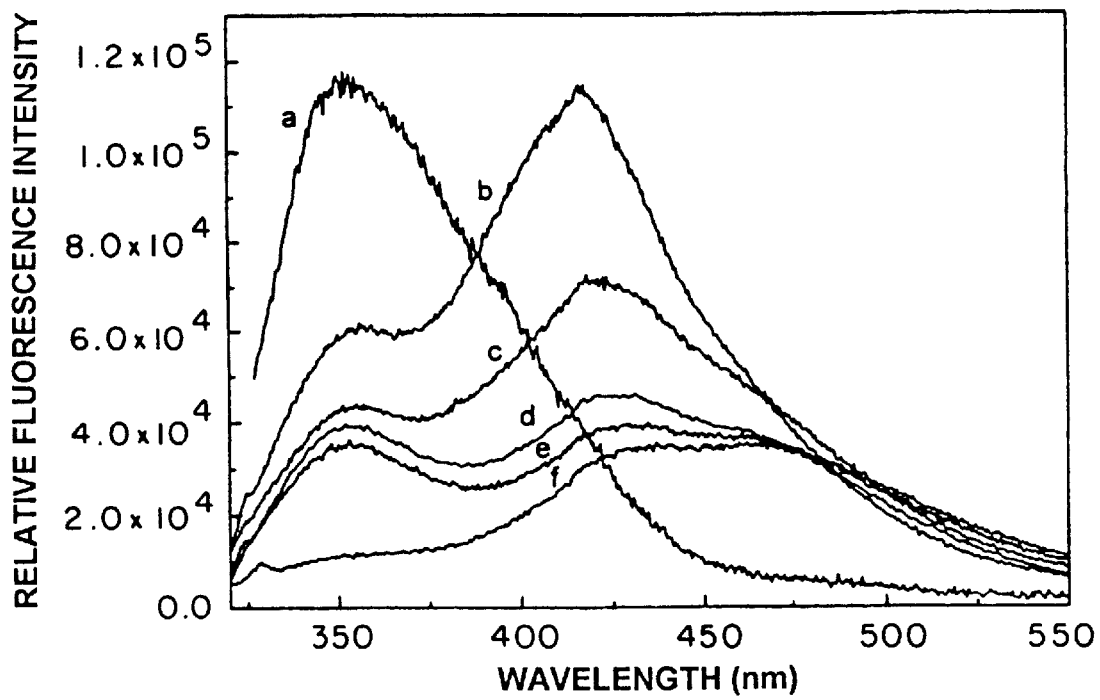
FIG. 3 is a graph showing relative fluorescent intensity vs wavelength for DMABN-Cyclam in n-hexane (line a), toluene (line b), tetrahydrofuran (line c), 2-propanol (line d), ethanol (line e), and water (line f). All concentrations were 25 $\mu$M, with the exception of n-hexane, whose low solubility made this concentration unattainable (the hexane emission has been normalized to that seen in toluene.

Solvent Dependence of Triple Fluorescence for DMABN-Cyclam. The UV spectra for DMABN-Cyclam in ethanol shows a single absorption peak at 295 nm. Excitation at this wavelength leads to three emission peaks: 352 nm, 429 nm, and 473 nm (FIG. 3). The fluorescence excitation spectra for these three emission wavelengths overlap at 295 nm, further indicating the purity of this compound and that each of these emission bands arise from excitation of the same ground state species. Intensity contributions and wavelength placement of the three excited state species were determined using a peak fitting protocol discussed in the experimental section. Because of the spectral overlap apparent between these three species, only qualitative information such as relative intensity trends and approximate peak positions have been derived from this analysis. The peak at 352 nm is attributed to the LE state emission of DMABN-Cyclam, and compares favorably to that found for DMABN in THF ($\lambda_{max}$=354 nm). Recl. Trav. Chim. Pays-Bas, 1995, 114, 517–527, the entirety of which is incorporated herein by reference for all purposes. Identification of the two additional, red-shifted emission peaks was accomplished by comparison to structural analogues of DMABN-Cyclam, DMABN-Crown5 and CNP3NM. Letard et. al. reported that DMABN-Crown5 exhibits a TICT emission that red-shifts and increases in intensity as the solvent polarity is increased from hexane (where the emission band was too weak to be measured accurately), to toluene ($\lambda_{max}$=406 nm), to acetonitrile ($\lambda_{max}$=466 nm). Id. Similarly, DMABN-Cyclam, which differs from DMABN-Crown5 primarily in the replacement of nitrogen binding sites for the oxygen atoms of the crown ether, reports a similar trend in the emission spectra (FIG. 3): hexane ($\lambda_{max}$=390 nm±10 nm), toluene ($\lambda_{max}$=413±10 nm) and ethanol ($\lambda_{max}$=473±3 mn). We, therefore, attribute the third emission band in ethanol at 473 nm to a TICT state. Unlike DMABN-Crown5, however, DMABN-Cyclam has two additional amine groups linked by a short chain (n=3 and n=4) to the benzonitrile acceptor. Petrov et. al., J. Phys. Chem., 1996, 100, 6368–6370, the entirety of which is incorporated herein by reference for all purposes, have shown that azacrown ethers can readily form intermolecular exciplexes with pyrene, for example. Despite the cyclic nature of the cyclam functional group in DMABN-Cyclam, this molecule exhibits sufficient flexibility to form a sandwich complex in the excited state that gives rise to an intramolecular exciplex peak (E) (FIG. 2). The peak position identified for the exciplex peak of DMABN-Cyclam in hexane ($\lambda_{max}$=392 nm±10 nm) compares favorably with that found for CNP3NM in isopentane ($\lambda_{max}$=390 nm). Van der Auweraer, M.; Vannerem, A.; de Schryver, F. C. J. Mol Struct., 1982, 84, 343–351, the entirety of which is incorporated herein by reference for all purposes.

Several trends are evident from FIG. 3 with regards to the effect of solvent polarity on the triple fluorescence of DMABN-Cyclam. The TICT emission band red-shifts by more than 80 nm and increases in intensity relative to the LE emission as solvent polarity is increased. The relative intensity of the TICT band increases with solvent polarity due to a stabilization of the charge separation. This type of behavior was also reported for DMABN-Crown4. The exciplex emission does not red-shift quite as severely (43 nm), due to a smaller dipole moment compared with the TICT configuration. The intensity of the TICT emission band increases relative to the exciplex emission with increasing solvent polarity. This feature can be attributed to 1) increased stabilization of the larger dipole moment evident in the TICT state; and 2) increased radiationless decay of the exciplex by internal conversion in the more polar solvents. In fact, the intensity of the intramolecular exciplex emission band is maximal in toluene, decreasing in intensity as the solvent polarity is increased. This type of behavior has been observed for other amine intramolecular exciplexes, including ((N,N-dimethylamino)-alkyl)phenanthrenes (Lewis, F. D.; Cohen, B. E. J. Phys. Chem., 1994, 98, 10591–10597, the entirety of which is incorporated herein by reference for all purposes) and ω-(1-pyrenyl)-α-N,N-dimethylaminoalkanes. Swinnenetal. J. Am. Chem. Soc., 1987, 109, 321–330, the entirety of which is incorporated herein by reference for all purposes. Knibbe et al. were the first to propose that the decrease in intermolecular exciplex fluorescence intensity with increasing solvent polarity was due to ionic dissociation and the formation of nonfluorescent radical ions in polar solvents. J. Chem. Phys., 1967, 47, 1184–1185, the entirety of which is incorporated herein by reference for all purposes. Because ionic dissociation is not possible in intramolecular exciplexes, Mataga and co-workers suggested that a compact folded geometry is favored in nonpolar solvents, and looser, more open geometries are apparent in polar solvents. Okada et al., J. Phys. Chem., 1981, 85, 3957–3960, the entirety of which is incorporated herein by reference for all purposes. The loose geometry is akin to the solvent-separated radical ion pair which is formed in intermolecular exciplexes, thereby explaining the quenching effect observed in more polar solvents. In a similar fashion, it is expected that prior to excitation DMABN-Cyclam will conform to a unique conformation in solvents of differing polarity. Presumably, DMABN-Cyclam optimally conforms to a compact folded configuration in toluene, fostering enhanced intramolecular exciplex formation and emission. As the polarity of the solvent is increased, solvation of the aza groups on the cyclam moiety is enhanced, allowing DMABN-Cyclam to attain a more open configuration that decreases intramolecular exciplex formation and emission. Similar behavior in other dye-linked aza crown ethers has been reported. Collins et al.,J. Chem. Soc. Chem. Comm., 1997, 12, 1135–1136, the entirety of which is incorporated herein by reference for all purposes.

Figure 4:
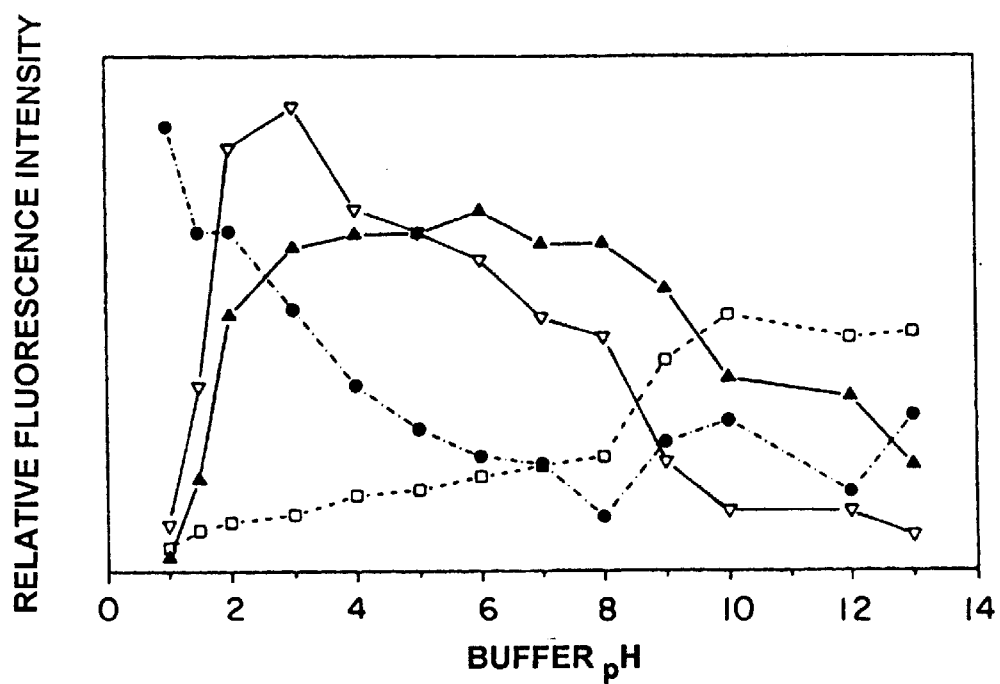
FIG. 4 is a graph showing the effect of pH on the triple fluorescence of DMABN-Cyclam in water: solid circles, LE; open squares, TICT/E; open triangles, E/LE; and solid triangles, TICT/LE.

The LE band exhibits an intensity minima in water because of the high polarity of this solvent, and its capability for stabilizing the two charge transfer complexes. The small hypsochromic shift evident in the LE band (5 nm) with decreasing solvent polarity indicates that minimal charge transfer exists for this excited state species prior to formation of the charge transfer states. It's possible that steric hindrance introduced by the cyclam moiety forces the diethyl amino group to rotate out of the plane of the phenyl acceptor group, resulting in lower mesomeric interaction between D and A. Support of this contention was found by Letard et. al., supra, who reported a calculated twist angle for DMABN-Crown5 of 18° (compared to 1° for DMABN) which was attributed to the repulsion of the large ring of the 5-azacrown ether by the ortho-hydrogens.

pH Dependence of Triple Fluorescence for DMABN-Cyclam. An improved understanding of the interplay between the three excited state species can be achieved by examining the change in fluorescence emission for DMABN-Cyclam with pH (FIG. 4). Examining first the effect of pH on intramolecular exciplex emission (open triangles), this band is maximal at pH 3, dropping off rapidly at more acidic pH, and decreasing in a nearly linear fashion at more basic pH values. The $pK_a$ values for cyclam have been measured by several workers, and are summarized by Bianchi et. al., Coord. Chem. Rev., 1991, 110, 17–113. At 25° C., there is reasonable agreement between the different measurements for $pK_1$ (11.6±0.16), $pK_2$ (10.44±0.23) and $pK_3$ (1.55±0.11). However, there is considerable variability in the values determined for the $pK_4$ (0.94–2.41) of cyclam. The benzonitrile aza group of DMABN-Cyclam will have the lowest $pK_a$ value due to the strong, electron-withdrawing nature of this group. By comparison to the $pK_a$'s recorded for aniline ($pK_a$=4.63) and diethylamine ($pK_a$=10.5), the $pK_a$ for this aza group are expected to be as much as four orders of magnitude lower than that found in cyclam, particularly since the nitrile functionality makes this group an even stronger acceptor. As the acidity drops below pH 2, DMABN-Cyclam will likely be triply protonated, causing intramolecular exciplex formation to decrease dramatically due to the inability of the protonated aza groups to donate charge to the phenyl acceptor group. As the pH increases above pH 3, the intramolecular exciplex emission band steadily decreases. This appears to be due to a shift in the equilibrium from the exciplex to the TICT state as the pH is increased. Evidence for this shift exists in a plot of the change in TICT/E versus pH (open squares, FIG. 4). In general, the TICT emission band slowly dominates the emission spectra as the pH increases, perhaps due to the fact that unlike the exciplex state, the charge transfer step for the TICT state formation requires no structural rearrangement.

The TICT emission band (closed triangles, FIG. 4), in similar fashion to the exciplex emission band, passes through a maximum at pH 3. However, the emission band for TICT is nearly level from pH 3–8, before steadily declining as the alkalinity is increased from pH 8–13. The decrease in TICT emission seen above pH 8 is attributed to an increase in quenching by the exciplex aza groups. The quenching of DMABN's TICT fluorescence has been reported by Wang et al. in the examination of a series of tertiary amines. Faraday Trans. 2, 1988, 84(11), 1809–1823, the entirety of which is incorporated herein by reference for all purposes. At pH values less than 2, DMABN-Cyclam will be triply protonated, and TICT state formation will decrease due to the decrease in charge transfer resulting from electrostatic repulsion with the three protonated nitrogens closely linked to the benzonitrile aza group.

The LE emission intensity (solid circles, FIG. 4) reported a steady decrease in intensity with increasing pH, ultimately leveling off at pH 8 and above. As DMABN-Cyclam is deprotonated and charge transfer facilitated, the equilibrium will shift towards the formation of the two charge-transfer states, E and TICT.

Effect of Metal Complexation on Triple Fluorescence of DMABN-Cyclam. Because the aza groups responsible for metal cation binding are also directly involved with the formation of the two charge-transfer excited state complexes (E and TICT), metal binding by DMABN-Cyclam should have a dramatic influence upon the fluorescence intensity of the triple fluorescence. A series of different metal cations were investigated in both protic (water, pH=7, Table 1) and aprotic solvents (acetonitrile, FIG. 5). In order to simplify the discussion, the metal ions have been classified as follows: 1) diamagnetic metal cations—$Zn^{2+}$ and $Cd^{2+}$; 2) paramagnetic metal cations—$Cu^{2+}$ and $Ni^{2+}$; and, 3) diamagnetic, heavy metal cations—$Hg^{2+}$ and $Pb^{2+}$.

TABLE 1

Relative Change in LE, E, and TICT Emission Observed for the Addition of 12 µM of Each Metal Salt to a 25 µM Solution of DMABN-Cyclam in Buffered Water (pH = 7)

| Metal ion | LE | E | TICT |
| --- | --- | --- | --- |
| none | 0.54 | 1.2 | 1.4 |
| Zn(II) | 2.2 | 1 | 1.2 |
| Cd(II) | 0.68 | 1.1 | 1.4 |
| Cu(II) | 0.42 | 0.9 | 1.2 |
| Ni(II) | 0.43 | 0.94 | 1.2 |
| Pb(II) | 0.51 | 1.1 | 1.4 |
| Hg(II) | 0.51 | 0.93 | 1.2 |

Consider first the situation evident for DMABN-Cyclam dissolved in water. As was mentioned earlier, DMABN-Cyclam likely conforms to an open geometry in this strongly polar solvent, a conformation lowering the extent of exciplex and LE emission, while favoring TICT state formation. Complexation of metal cations by DMABN-Cyclam in water (Table 1) causes a net decrease in the TICT and E state emission. Complexation of the cyclam aza groups by metal cations lowers the extent of charge transfer possible with the benzonitrile acceptor group, and hence, diminishes each of these charge transfer emission bands. In conjunction with the equilibrium shown in FIG. 2, as the TICT and E concentrations decrease, the LE emission increases. This was, in fact, observed for the diamagnetic metal cations, $Zn^{2+}$ and $Cd^{2+}$, however, the paramagnetic and heavy metal cations caused a decrease in the LE emission following complexation. Paramagnetic (Varnes et al., J. Am. Chem. Soc., 1972, 94, 946–950) and large or easily reducible cations (Akkaya et al., J. Am. Chem. Soc., 1990, 112, 3590–3593) are recognized for their intracomplex, quenching behavior, and, apparently, are responsible for the decrease observed in LE emission.

Figure 5:
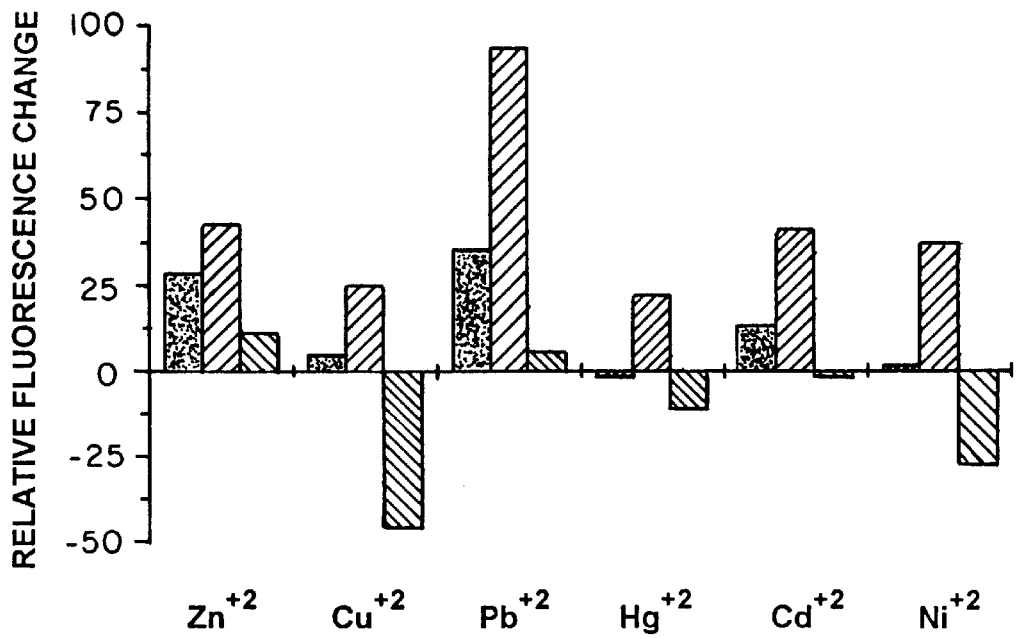
FIG. 5 shows the relative change in LE (solid), E (diagonal lines), and TICT (hatched lines) emission summarized for addition of 12 $\mu$M of each metal salt to a 25 $\mu$M solution of DMABN-Cyclam. in acetonitrile.
Figure 6:
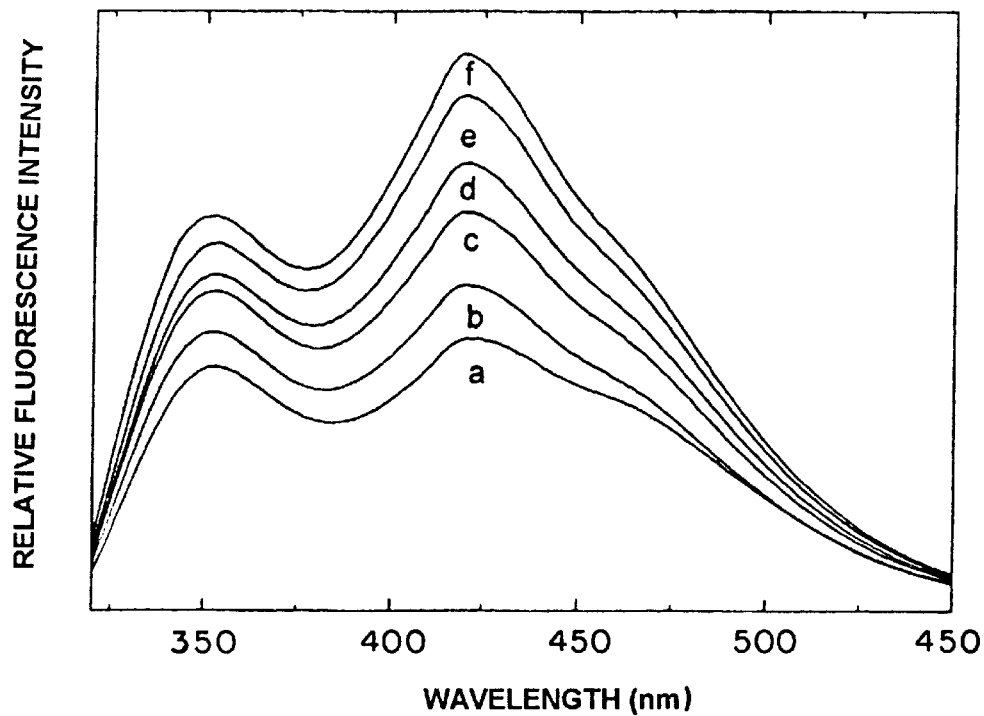
FIG. 6 shows the influence of $Zn^{2+}$ addition on the triple fluorescence of a 25 $\mu$M solution of DMABN-Cyclam in acetonitrile: (a) 0 $\mu$M, (b) 6.2 $\mu$M, (c) 12 $\mu$M, (d) 18 $\mu$M, (e) 25 $\mu$M, and (f) 37 $\mu$M.

A completely different set of results are obtained when the aprotic solvent, acetonitrile, is used for the metal complexation studies. Summarized in FIG. 5 are the relative changes seen for LE (solid), E (diagonal lines) and TICT (hatched lines) emission following the addition of 12 µM of each metal salt to a 25 µM solution of DMABN-Cyclam in acetonitrile. Shown in FIG. 6 is an example set of emission spectra indicating the influence of $Zn^{2+}$ addition on the triple fluorescence of DMABN-Cyclam in acetonitrile. The most dramatic difference realized from the situation observed in water, is that in all cases, complexation of metal cations by DMABN-Cyclam caused an increase in the exciplex emission. This result is surprising, considering that complexation of the exciplex aza group would normally be expected to reduce the extent of charge transfer and, hence, lower the exciplex emission intensity. Because the intramolecular exciplex emission does not decrease, it can be concluded that in acetonitrile, the nitrogen involved in exciplex formation is no longer complexed with the metal cation. This contention is also supported by the absence of any blue-shifting seen in the exciplex emission. As was concluded previously from the study of DMABN-Cyclam in solvents of varying polarity, DMABN-Cyclam forms a more compact, folded geometry in acetonitrile wherein the exciplex aza group apparently does not participate in the complexation of the metal cation. Apparently, complexation of a metal cation by the three remaining nitrogens provides enough shielding to slow electron transfer from the benzonitrile radical anion moiety. The dominating influence on the exciplex emission band arises from the elimination of quenching amines due to the interaction of the remaining three aza groups with the complexed metal cation. Additionally, binding of the metal cation may result in a new, metal/ligand, complex geometry that further favors exciplex formation.

Figure 7:
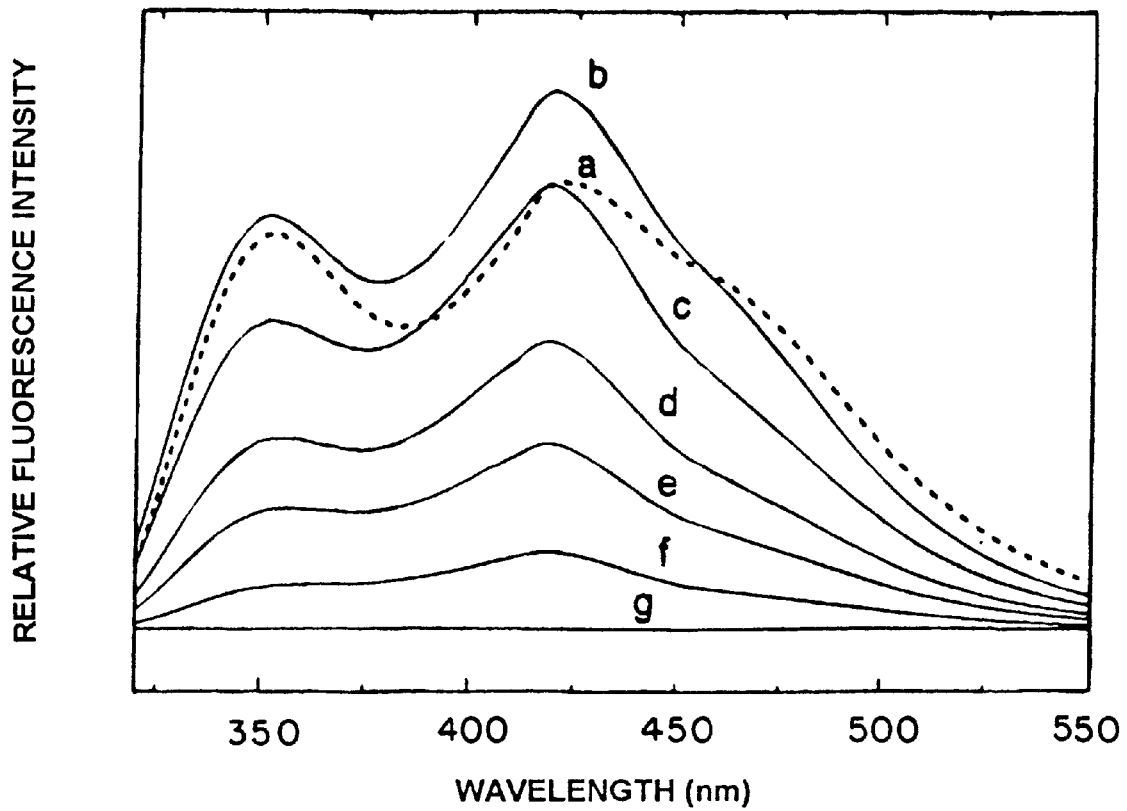
FIG. 7 shows the influence of $Cu^{2+}$ addition on the triple fluorescence of a 25 $\mu$M solution of DMABN-Cyclam in ethanol: (a) 0 $\mu$M, (b) 12 $\mu$M, (c) 74 $\mu$M, (d) 149 $\mu$M, (e) 223 $\mu$M, (f) 372 $\mu$M, and (g) 1880 $\mu$M.

Reduction in the charge transfer character of the TICT aza group due to binding of a metal cation in the ground state will result in at least three effects: 1) providing that the exciplex aza group is not partaking in metal cation complexation, the exciplex emission will increase when quenching from the TICT aza group is reduced; 2) TICT emission will decrease along with the reduced capability for the complexed aza group to donate charge to the benzonitrile acceptor group; and, 3) the LE emission band will increase with the shift in equilibrium from TICT to LE. The only exception to the expected increase in LE emission was found for the metal cation, $Hg^{2+}$. This reduction in emission intensity is attributed to the quenching behavior of this large and easily reducible metal cation. For higher concentrations of paramagnetic metal ions, such as $Cu^{2+}$, there is the additional impact of uncomplexed metal ions causing diffusional quenching of the [DMABN-Cyclam:Metal ion] complex. This is shown in FIG. 7, which plots the change in triple fluorescence seen for the sequential addition of $Cu^{2+}$ to DMABN-Cyclam in acetonitrile. As the concentration of copper cations becomes greater than the equimolar concentration of DMABN-Cyclam (25 $\mu$m), the overall triple emission intensity can be observed to decrease in intensity due to quenching. The paramagnetic effect is weak enough for this system that it is not observed until the addition of greater than a stoichiometric amount of $Cu^{2+}$. This effect is perhaps related to a small coefficient of the benzonitrile LUMO on the amino nitrogen complexed with the $Cu^{2+}$.

Obviously, many modifications and variations of the present invention are possible in light of the above teachings. It is therefore to be understood that, within the scope of the appended claims, the invention may be practiced otherwise than as specifically described.

What is claimed is:

1. A compound of the formula:

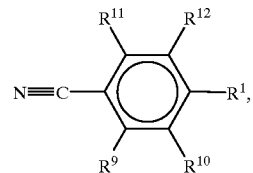

wherein $R^1$ is:

a group having the formula:

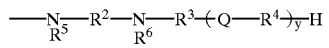

wherein $R^2$ and $R^3$ are unsubstituted $C_2$ to $C_4$ alkylene groups or $C_2$ to $C_4$ alkylene groups substituted with an aliphatic group, and may be the same as or different from one another;

$R^4$ is -, an unsubstituted $C_2$ to $C_4$ alkene group, or a $C_2$ to $C_4$ alkylene group substituted with an aliphatic group, and may be the same or different from any other $R^4$ groups present and may be the same or different from $R^2$ and $R^3$;

Q is NH, $NR^7$, or O, and may be the same as or different from any other Q group present;

$R^5$, $R^6$, and $R^7$ are aliphatic groups and may be the same as or different from each other, and y is an integer having a value of from 1 to 5;

or an azacyclo group having at least two ring nitrogens, at least one of said ring nitrogens being substituted by said benzonitrile group and at least one of said ring nitrogens being 2 to 4 carbon atoms from said benzonitrile-substituted ring nitrogen, said azacyclo group having as ring members at least one additional heteroatom selected from the group consisting of N, O, and S, said at least one additional heteroatom having at least 2 carbons between it and the nearest of other ring member heteroatoms; and $R^9$, $R^{10}$, $R^{11}$, and $R^{12}$ are H or $CH_3$ and may be the same as or different from each other;

wherein said compound exhibits fluorescent emission at a first set of three separate emission bands in response to a light at an excitation wavelength in the absence of a metal ion and at a second set of three separate emission bands in the presence of said metal ion, the difference between said first and second set of three separate emission bands being characteristic of said metal ion.

2. The compound of claim 1, wherein said azacyclo group is ring-saturated.

3. The compound of claim 1, wherein $R^1$ is

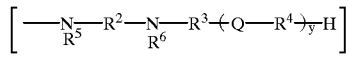

or an azacyclo group of the following:

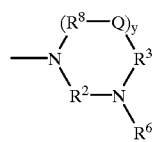

$R^2$ and $R^3$ of said azacyclo group are unsubstituted $C_2$ to $C_4$ alkylene groups or $C_2$ to $C_4$ alkylene groups substituted with an aliphatic group, and may be the same as or different from one another;

Q of said azacyclo group is NH, $NR^7$, O, or S, and may be the same as or different from any other Q group present in said azacyclo group;

$R^6$ of said azacyclo group and $R^7$ of said Q in said azacyclo group are aliphatic groups and may be the same as or different from each other;

$R^8$ of said azacyclo group is an unsubstituted $C_2$ to $C_4$ alkylene group or a $C_2$ to $C_4$ alkylene groups substituted with an aliphatic group, and may be the same as or different from any other $R^8$ group present in said azacyclo group; and y of said azacyclo group is an integer having a value of from 1 to 5.

4. The compound of claim 3, wherein y of said azacyclo group is one.

5. The compound of claim 3, wherein Q of said azacyclo group is N.

6. The compound of claim 5, wherein y of said azacyclo group is two.

7. The compound of claim 3, wherein at least one $R^8$ of said azacyclo group is —$CH_2CH_2$—.

8. The compound of claim 7, wherein y of said azacyclo group is two, Q of said azacyclo group is NH, $R^2$ of said azacyclo group is —$CH_2CH_2CH_2$—, $R^3$ of said azacyclo group is —$CH_2CH_2$—, $R^6$ of said azacyclo group is H, one $R^8$ of said azacyclo group is —$CH_2CH_2$—, and one $R^8$ of said azacyclo group is —$CH_2CH_2CH_2$—.

9. The compound of claim 1, wherein $R^5$, $R^6$, and $R^7$ are $C_1$ to $C_4$.

10. The compound of claim 1, wherein $R^2$, $R^3$, $R^5$, $R^6$, $R^7$, and $R^8$ are aliphatic amines, aliphatic alcohols, or aliphatic thiols.

11. The compound of claim 1, wherein $R^9$, $R^{10}$, $R^{11}$, and $R^{12}$ are H.

12. A method of detecting a metal ion in a liquid, comprising the steps of:

adding a compound of the formula:

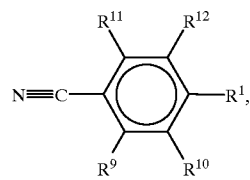

wherein $R^1$ is:

a group having the formula:

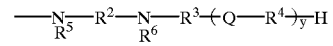

wherein $R^2$ and $R^3$ are unsubstituted $C_2$ to $C_4$ alkylene groups or $C_2$ to $C_4$ alkylene groups substituted with an aliphatic group, and may be the same as or different from one another;

$R^4$ is -, an unsubstituted $C_2$ to $C_4$ alkylene group, or a $C_2$ to $C_4$ alkylene group substituted with an aliphatic group, and may be the same or different from any other $R^4$ groups present and may be the same or different from $R^2$ and $R^3$;

Q is NH, $NR^7$, or O, and may be the same as or different from any other Q group present;

$R^5$, $R^6$, and $R^7$ are aliphatic groups and may be the same as or different from each other; and y is an integer having a value of from 1 to 5;

or an azacyclo group having at least two ring nitrogens, at least one of said ring nitrogens being substituted by said benzonitrile group and at least one of said ring nitrogens being 2 to 4 carbon atoms from said benzonitrile-substituted ring nitrogen, said azacyclo group having as ring members at least one additional heteroatom selected from the group consisting of N, O, and S, said at least one additional heteroatom having at least 2 carbons between it and the nearest of other ring member heteroatoms; and $R^9$, $R^{10}$, $R^{11}$, and $R^{12}$ are H or $CH_3$ and may be the same as or different from each other, to said liquid, wherein said compound exhibits fluorescent emission at a first set of three separate emission frequencies in response to a light at an excitation wavelength in the absence of said metal ion and at a second set of three separate emission bands in the presence of said metal ion, said first and second set of three separate emission frequencies being the same as or different from each other and wherein the difference between said first and second set of three separate emission bands is characteristic of said metal ion;

exposing said liquid including said compound to said light at said excitation wavelength;

detecting said fluorescent emission at least at one of said second three separate emission bands;

comparing said detecting fluorescent emission with a standard, whereby the presence of said metal ion is determined.

13. The method of claim 12, further comprising the step of comparing the fluorescent emission at least at one of said first set of frequencies in response to said excitation light in the absence of said metal ion with at least one of said second set of fluorescent emission frequencies in response to said excitation light in the presence of said metal ion.

14. The method of claim 13, comprising the step of comparing the fluorescent emission at least at two of said first set of frequencies in response to said excitation light in the absence of said metal ion with at least two frequencies of said second set of fluorescent emission frequencies in response to said excitation light in the presence of said metal ion.

15. The method of claim 14, comprising the step of comparing the fluorescent emission at said three frequencies of said first set of fluorescent emission frequencies in response to said excitation light in the absence of said metal ion with said three frequencies of said second set of fluorescent emission frequencies in response to said excitation light in the presence of said metal ion.

16. The method of claim 12, wherein said liquid is an aqueous solvent for said metal ion.

17. The method of claim 12, wherein said liquid is a nonaqueous solvent for said metal ion.

18. The method of claim 12, wherein said liquid is selected from the group consisting of ethanol, acetonitrile, $H_2O$, and mixtures thereof.

19. The method of claim 12, wherein said metal ion is selected from the group consisting of transition metal ions, heavy metal ions, and mixtures thereof.

20. The method of claim 19, wherein said metal ion is selected from the group consisting of Zn(II), Cd(II), Cu(I), Cu(II), Ni(II), Pb(II), Hg(II), Fe(III), Al(III), and mixtures thereof.

* * * * *

UNITED STATES PATENT AND TRADEMARK OFFICE
CERTIFICATE OF CORRECTION

PATENT NO. : 6,143,569
DATED : November 7, 2000
INVENTOR(S) : Collins et al.

Figure 1A:
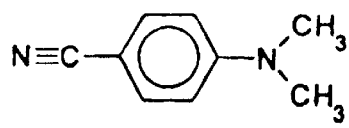
FIG. 1a through FIG. 1d show various fluorophores discussed in this specification.
Figure 1B:
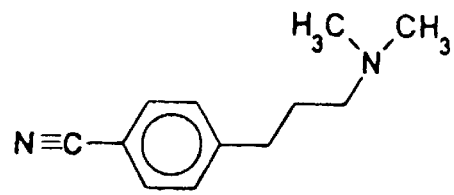
Figure 1C:
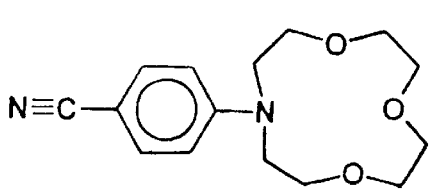
Figure 1D:
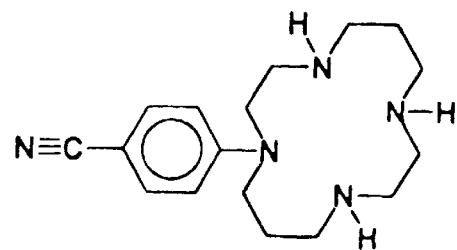

It is certified that error appears in the above-identified patent and that said Letters Patent is hereby corrected as shown below:

On Drawing Sheet 1, please delete "PRIOR ART" from Fig. 1d.

Signed and Sealed this

Eighteenth Day of September, 2001

*Attest:*

*Nicholas P. Godici*

*Attesting Officer*

NICHOLAS P. GODICI
*Acting Director of the United States Patent and Trademark Office*